United States Patent
Feder

(10) Patent No.: US 6,782,557 B1
(45) Date of Patent: Aug. 31, 2004

(54) UNDERGARMENT WITH A POLYMER COATED FABRIC LAYER FOR PROTECTION AGAINST INCONTINENCE

(75) Inventor: Robert L. Feder, Pleasanton, CA (US)

(73) Assignee: Dribrief, Inc., Grover Beach, CA (US)

( * ) Notice: Subject to any disclaimer, the term of this patent is extended or adjusted under 35 U.S.C. 154(b) by 0 days.

(21) Appl. No.: 10/393,939

(22) Filed: Mar. 20, 2003

(51) Int. Cl.$^7$ ................................................. A41B 9/00
(52) U.S. Cl. ..................................... 2/400; 2/403; 2/406
(58) Field of Search ...................... 2/400–408, 113–115, 2/81, 82, 243.1, 73, 78.1–78.4; 604/385.01–396; 442/79; 427/434.2

(56) References Cited

U.S. PATENT DOCUMENTS

| | | | | |
|---|---|---|---|---|
| 3,237,625 A | * | 3/1966 | Johnson | 604/396 |
| 3,613,687 A | * | 10/1971 | Kennedy | 604/396 |
| 4,351,340 A | * | 9/1982 | McLeod | 2/406 |
| 4,573,987 A | * | 3/1986 | Lamb, Jr. | 604/396 |
| 5,155,867 A | * | 10/1992 | Norvell | 2/113 |
| 6,379,753 B1 | * | 4/2002 | Soane et al. | 427/434.2 |

* cited by examiner

Primary Examiner—Gloria M. Hale
(74) Attorney, Agent, or Firm—The Kline Law Firm

(57) ABSTRACT

An undergarment that provides protection against mild to moderate incontinence by using a layer of hydrophilic fabric placed in an absorption region. The fabric most commonly used will be sheared terry cloth. The terry cloth is treated with a strongly hydrophobic polymer material to form a chemical barrier so that moisture will not readily pass through the cloth. This absorptive panel is then simply sewn into conventional undergarments.

7 Claims, 4 Drawing Sheets

UNDERGARMENT WITH A POLYMER COATED FABRIC LAYER FOR PROTECTION AGAINST INCONTINENCE

BACKGROUND OF THE INVENTION

1. Field of the Invention

The present invention relates generally to medical and personal hygiene devices, and more particularly is an undergarment that with a specialized fabric treatment that protects the wearer against mild to moderate incontinence using a layer of polymer treated fabric.

2. Description of the Prior Art

This invention is directed to resolution of the problem of minor to moderate incontinence, i.e. the inability to completely control one's bladder. There are over 10 million people in the United States alone who suffer from some level of incontinence. A problem of this magnitude has of course led to prior art solutions.

The current art solution most commonly used for the problem of minor to moderate incontinence is illustrated in FIG. 1. This product is an undergarment that uses a design with a pouch 1 that keeps a man's penis centered on the moisture absorbing panel. This is of course not the ultimate in comfort for the user of the device. However, the possibly more significant drawback to the prior art design is the number of layers of fabric that are required. As shown in FIG. 2, next to the wearer's skin 2, there is a first liner 3. On top of the liner is a wicking fabric layer 4, and then a transport insert layer 5 on top of that. On top of the transport layer 5, an absorbent layer 6 receives the moisture 7. Finally, to shield the wearer's clothing from moisture 7 seeping through the absorbent layer 6, there is an outer shield 8. These five layers of fabric render the device quite bulky, and very different in appearance from normal underwear. The prior art devices have a distinctly "diaperish" or incontinence controlling appearance.

Accordingly, it is an object of the present invention to provide an undergarment that uses a minimal number of layers of fabric.

It is another object of the present invention to provide an undergarment that is natural in appearance, that is, an undergarment that does not appear to be a device to protect against incontinence.

It is still another object of the present invention to provide an undergarment that is comfortable for the wearer.

It is yet another object of the present invention to provide an undergarment that is fully machine washable.

SUMMARY OF THE INVENTION

The present invention is an undergarment that provides protection against mild to moderate incontinence. For female wearers, the absorbing panel not only provides incontinence protection, but can be used for absorbing discharges as a result of beginning and final stages of a women's menstrual cycle.

The undergarment comprises an absorptive panel formed with a layer of hydrophilic fabric treated on one side with a permanent or semi-permanent hydrophilic polymer solution. Alternatively, a hydrophilic fabric combined with a specialized fabric treated with a hydrophobic polymer solution may be utilized to form the absorptive layer. The hydrophilic fabric most commonly used will be terry cloth. The absorptive panel formed with the hydrophilic fabric is then integrated into conventional undergarments.

An advantage of the present invention is that it significantly reduces the number of layers of fabric required to protect against incontinence.

Another advantage of the present invention is that the reduced number of layers of fabric reduces the heat retention of the undergarment, making the undergarment more comfortable for the wearer.

Another advantage of the present invention is that the appearance of the device does not differ significantly from normal underwear.

A still further advantage of the present invention is that the undergarment has a useful life equal to that of normal underwear.

These and other objects and advantages of the present invention will become apparent to those skilled in the art in view of the description of the best presently known mode of carrying out the invention as described herein and as illustrated in the drawings.

DETAILED DESCRIPTION OF THE INVENTION

Figure 1:
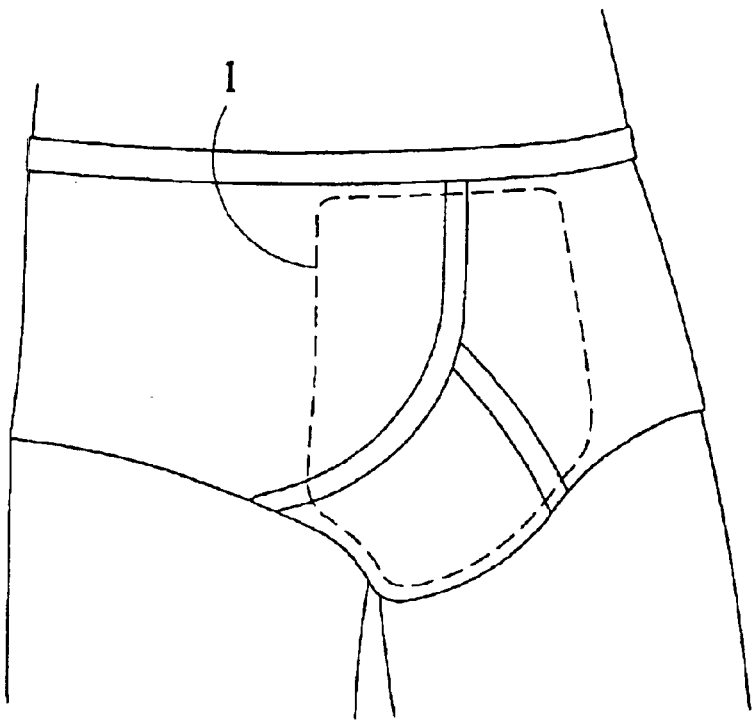
FIG. 1 is a front perspective view of a common prior art undergarment designed to protect against incontinence.
Figure 2:
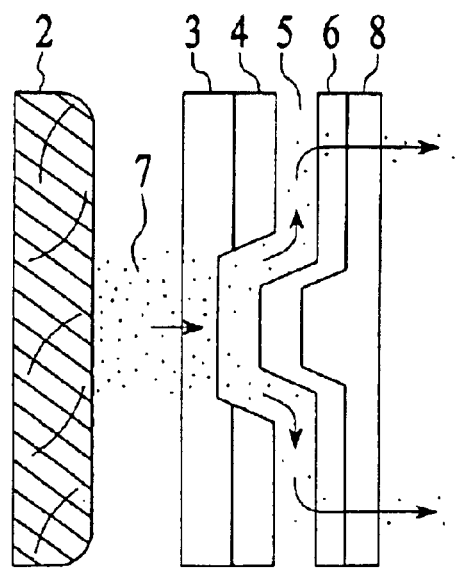
FIG. 2 is a schematic sectional view of the prior undergarment.
Figure 3:
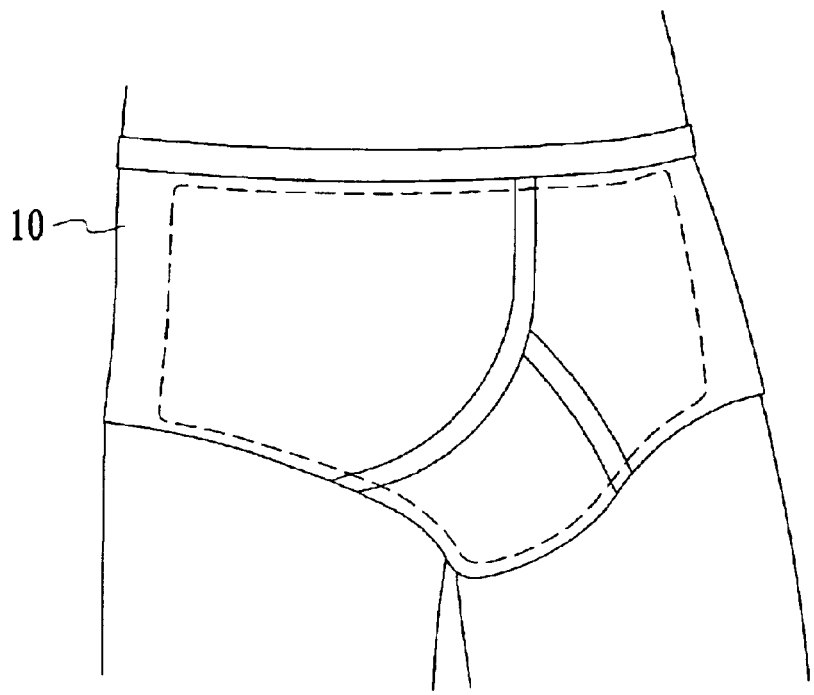
FIG. 3 is a front perspective view of an undergarment constructed according to the present invention.

The present invention is a protective undergarment 10 that provides protection against mild to moderate incontinence. The undergarment 10 comprises a absorptive panel formed with a layer of hydrophilic fabric 12 that is treated with a hydrophobic polymer chemical barrier layer 14. The hydrophilic fabrics 12 most commonly used for the absorptive panel will be a cotton terry fabric or a cotton and polyester terry fabric.

To prepare the fabric 12 for use in the protective undergarment 10, the fabric 12 is treated with a strongly hydrophobic chemical barrier layer 14. The chemical barrier layer 14 prevents moisture from readily passing through the absorptive panel of the undergarment. In the preferred embodiment, the chemical barrier layer 14 is a polymer such as NANO-PEL from NANO-TEX. Two methods can be used to create the absorptive panel: If a single layer of fabric is to be used, the fabric 12 will be a terry cloth sheared on one side to accept the hydrophobic chemical treatment. If a two-layer absorptive panel is to be used, the fabric 12 will be a terry cloth attached to a second fabric 20 such as a cotton or polyester jersey that has been treated with the hydrophobic chemical.

Figure 4:
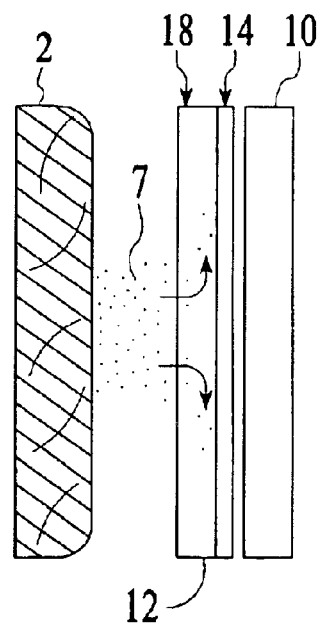
FIG. 4 is a schematic view of an undergarment with a single layer absorptive panel constructed according to the present invention.

FIG. 4 illustrates the absorptive panel formed with a single fabric layer 12. After the chemical barrier layer 14 has been added to the terry cloth 12, the result is a fabric panel 16 with two sides, each side having very distinct characteristics. A first, untreated side 18 (the side nearest the wearer's skin 2) of the terry fabric 12 is very hydrophilic so that moisture is drawn into the fabric 12. The outer side of the fabric 12 is the side treated with the chemical barrier layer 14. The chemical barrier layer 14 is strongly hydrophobic, so that moisture 7 does not pass through the barrier layer 14. Accordingly, the moisture 7 is retained in the terry fabric 12 until the protective undergarment 10 is laundered.

Figure 5:
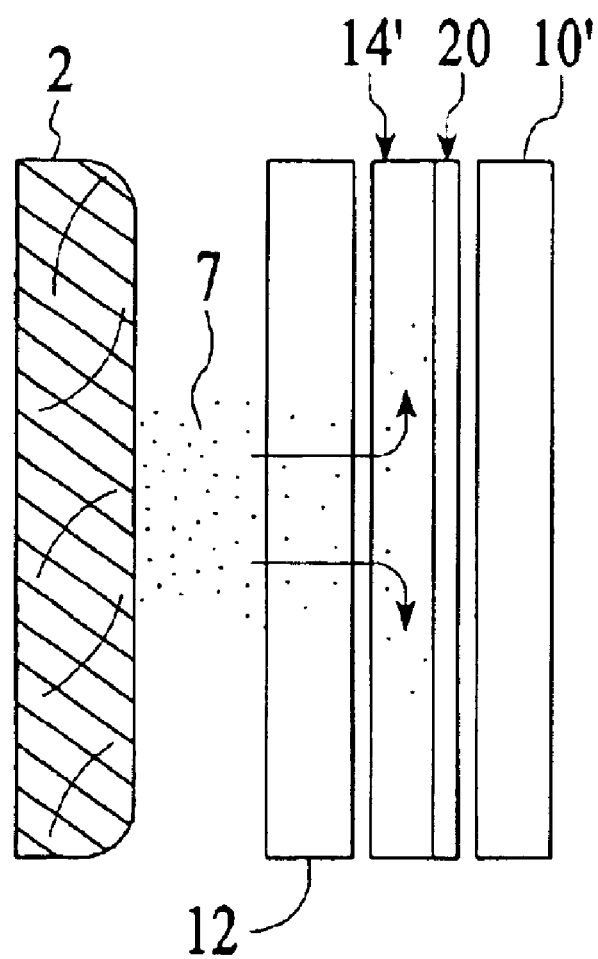
FIG. 5 illustrates an undergarment with a double layer absorptive panel constructed according to the present invention.

FIG. 5 shows the absorptive panel formed with two layers of fabric. In this application, a second layer of cloth 20 is used to provide the barrier layer 14' between an untreated cotton terry fabric absorption panel 12 and the fabric of the main body of the undergarment 10'. The cloth 20 is treated with the polymer coating to render the cloth 20 hydrophobic. The cloth 20 will typically be cotton or polyester woven or knitted jersey fabric, and will be laminated to the terry cloth panel 20 to secure the panels in position.

While this alternate construction does introduce a second layer of material, it allows for the use of terry looped on both sides (not sheared on one side as in the one-layer construction) for greater moisture absorbency, that may be required for more severe incontinence.

In light of the need for laundering of the undergarment 10, it should be noted that the treated chemical barrier 14 being positioned between the hydrophilic terry 12 and the conventional undergarment protects the chemically treated hydrophobic barrier 14 for the life of the garment.

Figure 6:
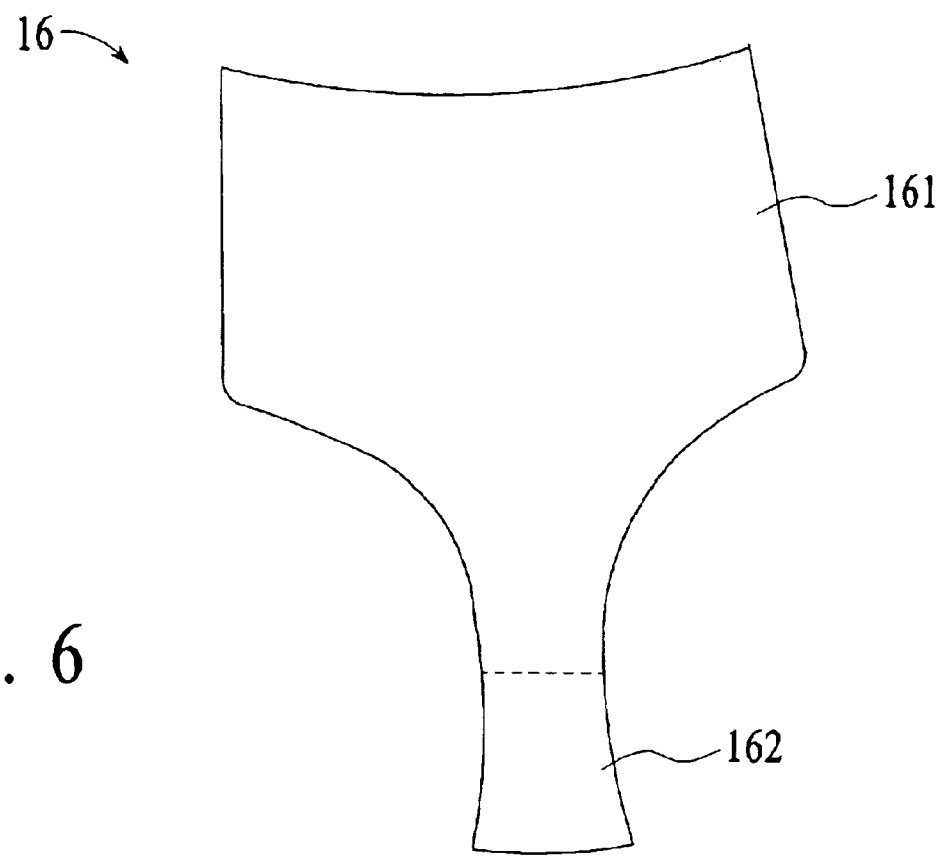
FIG. 6 shows a typical male absorptive panel constructed according to the present invention.
Figure 7:
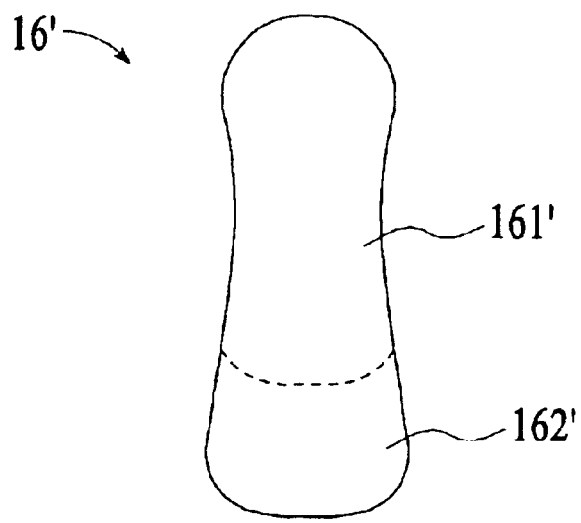
FIG. 7 shows a typical female absorptive panel constructed according to the present invention.

To construct the protective undergarment 10, following preparation of the absorptive panel, the treated panel is simply sewn into a conventional undergarment. The absorptive panel 16 is shaped as shown in FIG. 5 for the male version of the protective undergarment 10, and as in FIG. 6 for the female version 16'. The absorptive panels 16, 16' are each formed with a main front absorbent section 161, 161'. If desired, the panels 16, 16' can include an extended section 162, 162' that covers the rectal area of the wearer to protect against mild rectal incontinence. The panels 16, 16' can of course be contoured as desired to comfortably fit into any style of undergarment.

It should be noted that an alternate construction of the undergarment 10 is to treat the inner side of the base fabric of the undergarment with the polymer barrier, as opposed to treating the outer side of the fabric 12. The end result is essentially the same—a polymeric hydrophobic barrier layer sandwiched between an inner hydrophilic layer and an outer base fabric layer—but the manufacturing process is less efficient.

The above disclosure is not intended as limiting. Those skilled in the art will readily observe that numerous modifications and alterations of the device may be made while retaining the teachings of the invention. Accordingly, the above disclosure should be constructed as limited only by the restrictions of the appended claims.

I claim:

1. A protective undergarment comprising:

a hydrophilic absorbing fabric panel sewn into an interior of material constituting a body of an undergarment at a frontal location of said undergarment, and a hydrophobic barrier layer between said fabric panel and said material constituting said body of said undergarment; such that said protective undergarment provides protection against incontinence for a wearer with a minimal number of layers of fabric; wherein said hydrophobic barrier layer is a chemical treatment applied to said fabric panel.

2. The protective undergarment of claim 1 wherein:

said fabric panel is formed from cotton terry fabric.

3. The protective undergarment of claim 1 wherein:

said fabric panel is formed from a fabric sheared on one side.

4. The protective undergarment of claim 1 wherein:

said hydrophobic barrier layer is affixed to an outer side of said fabric panel.

5. The protective undergarment of claim 1 wherein:

said hydrophobic barrier layer is affixed to an inner side of said material constituting said body of said undergarment.

6. The protective undergarment of claim 1 wherein:

said hydrophobic barrier layer is a cloth chemically treated to render said cloth hydrophobic.

7. The protective undergarment of claim 1 wherein:

said cloth forming said hydrophobic barrier layer is jersey.

* * * * *